US007309495B2

(12) United States Patent
Foley et al.

(10) Patent No.: US 7,309,495 B2
(45) Date of Patent: Dec. 18, 2007

(54) HEMORRHAGIC FELINE CALICIVIRUS

(75) Inventors: Janet E. Foley, Davis, CA (US); Kate Hurley, Davis, CA (US); Niels C. Pedersen, Winters, CA (US)

(73) Assignee: The Regents of the University of California, Oakland, CA (US)

( * ) Notice: Subject to any disclaimer, the term of this patent is extended or adjusted under 35 U.S.C. 154(b) by 575 days.

(21) Appl. No.: 10/388,837

(22) Filed: Mar. 14, 2003

(65) Prior Publication Data

US 2004/0180064 A1 Sep. 16, 2004

(51) Int. Cl.
*C12N 7/00* (2006.01)

(52) U.S. Cl. ................................ 424/216.1; 435/235.1

(58) Field of Classification Search ..................... None
See application file for complete search history.

(56) References Cited

U.S. PATENT DOCUMENTS

| | | | | |
|---|---|---|---|---|
| 3,937,812 | A | 2/1976 | Bittle et al. | |
| 3,944,469 | A | 3/1976 | Bittle et al. | |
| 3,992,520 | A | 11/1976 | Gwatkin | |
| 4,522,810 | A * | 6/1985 | Pedersen | 424/216.1 |
| 4,795,634 | A | 1/1989 | Grimes et al. | |
| 5,716,822 | A | 2/1998 | Wardley et al. | |
| 5,718,901 | A | 2/1998 | Wardley et al. | |
| 5,785,968 | A | 7/1998 | Kimachi et al. | |
| 5,916,768 | A | 6/1999 | Dean | |
| 5,989,550 | A | 11/1999 | Harris et al. | |
| 6,231,863 | B1 | 5/2001 | Colau et al. | |
| 6,355,246 | B1 | 3/2002 | Kruger et al. | |

OTHER PUBLICATIONS

Pedersen et al., An isolated epizootic of hemorrhagic-like fever in cats caused by a novel and highly virulent strain of feline calicivirus. Veterinary Microbiology, 2000, vol. 73, p. 281-300.*

Johnson, R.P. (1992). "Antigenic Change in Feline Calicivirus During Persistent Infection," *Can J Vet Res* 56:326-330.

Pederson, N.C. et al. (2000). "An isolated epizootic of hemorrhagic-like fever in cats caused by a novel and highly virulent strain of feline calicivirus," *Veterinary Microbiology* 73:281-300.

Reubel, G.H. et al. (1992). "Acute and Chronic Faucitis of Domestic Cats—A Feline Calicivirus-Induced Disease," *Veterinary Clinics of North America: Small Animal Practice* 22(6):1347-1360.

Studdert, M.J. (1978). "Caliciviruses—Brief Review," *Archives of Virology* 58:157-191.

<http://www.pandecats.com/x/calici_outbreak_warning.htm> "Outbreak of Calicivirus in Los Angeles, California," visited on Jun. 17, 2003, 2 pages.

<http://www.vetmed.ucdavis.edu/CCAH/Prog-ShelterMed/news.htm> "Focal outbreak of an unusually virulent strain of feline calicivirus," visited on Jun. 17, 2003, 4 pages.

<http://www.vetmed.ucdavis.edu/whatsnew/article.cfm?id=1178> "School of Veterinary Medicine investigates rare virus outbreak in cats," visited on Jun. 17, 2003, 2 pages.

Afzalpurkar, Abhijit, et al.; "Induction of native protein reactive antibodies by immunization with peptides containing linear B-cell epitopes defined by anti-porcine ZP3β monoclonal antibodies"; *Journal of Reproductive Immunology* 1997 pp. 113-125 vol. 33.

Bagavant, Harini, et al.; "Autoimmune Ovarian Inflammation Triggered by Proinflammatory (Th1) T Cells is Compatible with Normal Ovarian Function in Mice"; *Biology of Reproduction* 1999 pp. 635-642 vol. 61.

Foster, James, A., et al.; "AM67, a Secretory Component of the Guinea Pig Sperm Acrosomal Matrix, is Related to Mouse Sperm Protein sp56 and the Complement Component 4-binding Proteins"; *The Journal of Biological Chemistry* 1997 pp. 12714-12722 vol. 272 No. 19.

Prasad, S.V., et al.; "Molecular biology approaches to evaluate species variation in immunogenicity and antigenicity of zone pellucida proteins"; *Journal of Reproduction and Fertility Supplement* 1996 pp. 143-149 vol. 50.

L11000/PIGZP3 Genbank entry Oct. 7, 1994 polynucleotide sequence encoding ZP protein.

Hurley, Kate F. et al.; "An outbreak of virulent systemic feline calicivirus disease"; 2004, *Journal of the American Veterinary Medical Association*, vol. 224, No. 2, pp. 241-249.

Schorr-Evans, E.M. et al.; "An epizootic of highly virulent feline calicivirus disease in a hospital setting in New England"; 2003, *Journal of Feline Medicine and Surgery*, vol. 5, pp. 217-226.

Verdon, Dan; "UC-Davis mounts investigation of rare calicivirus"; 2002, *DVM Advanstar Health Publication*; vol. 1, pp. 38-39.

* cited by examiner

*Primary Examiner*—Bruce R. Campell
*Assistant Examiner*—Agnieszka Boesen
(74) *Attorney, Agent, or Firm*—Townsend & Townsend & Crew LLP

(57) ABSTRACT

The present invention relates to a vaccine for immunization against a viral infection caused by a hemorrhagic feline calicivirus (hFCV), a novel, a typical and unusually virulent form of a calicivirus that results in a highly contagious and fatal hemorrhagic fever syndrome. The present invention further encompasses methods of immunizing cats against particular strains of hFCV.

7 Claims, No Drawings

HEMORRHAGIC FELINE CALICIVIRUS

BACKGROUND OF THE INVENTION

Feline calicivirus (FCV) is a common pathogen found in cats. This virus is often detected in multiple cat environments such as shelters and catteries. Feline calicivirus (FCV) infection can cause a variety of manifestations and symptoms including fever, upper respiratory signs, acute or chronic oral disease, limping, and occasionally pneumonia. Vaccination with an attenuated live virus against FCV is widely practiced, and affords moderate protection against acute disease caused by many, but not all, strains of calicivirus. Cats in FCV endemic populations may shed FCV in ocular and nasal discharge, saliva, and feces without showing clinical signs of infection. Such carrier cats may serve as a source of infection for others. In the past, feline caliciviral infection was not usually fatal, however, when death occurred it was most often due to pneumonia or severe upper respiratory infection in young kittens.

FCV infection and disease occur in acute and chronic forms (Studdert, M. J. (1978) *Arch. Virol.,* 58:157-191; Reubel et al., (1992) *Vet. Clin. No. Am. Small Anim. Pract.,* 22:1347-1360), wherein the manifesting signs of acute disease depend on the route (e.g., oral, aerosol) and the strain of virus. The disease may differ in severity, with more virulent strains causing fever; depression; dyspnea; pneumonia; and vesicles and ulcers of the tongue, hard palate and nostrils. Lower virulence strains are less likely to affect the lungs, although other signs are similar. Most FCV carriers are asymptomatic, however, a small proportion will develop a distinct disease syndrome known as chronic plasmacytic or lymphocytic stomatitis or chronic ulceroprolifereative stomatitis (Reubel et al. (1992) supra). This chronic oral disease is progressive and difficult to treat and is perhaps the most prevalent clinical manifestation of FCV as known. Although recognized strains of FCV have not been associated with significant acute mortality, the calicivirus genome is known to be highly mutable (Johnson, R. P., (1992) *Can. J. Vet. Res.,* 56:326-330). Thus, more highly virulent strains may arise at any time.

BRIEF SUMMARY OF THE INVENTION

The present invention relates to a vaccine and methods for immunization against a viral infection caused by a hemorrhagic feline calicivirus, designated hFCV, a novel, a typical and unusually virulent form of a calicivirus that results in a highly contagious and fatal hemorrhagic fever syndrome.

One aspect of the present invention provides an immunogenic composition for immunization against a viral infection caused by a hemorrhagic feline calicivirus (hFCV), wherein the composition comprises an immunologically effective amount of the hFCV and a physiologically acceptable carrier. Examples of the hFCV include, but are not limited to, strains such as FCV-Kaos and FCV-Ari. Optionally, the composition includes an adjuvant. The hFCV strains may be killed, attenuated, or partially inactivated.

Another aspect of the invention provides for a method of immunizing a cat against a hemorrhagic feline calicivirus (hFCV) which comprises administering to the cat an immunologically effective dose of the composition comprising an immunologically effective amount of the hFCV and a physiologically acceptable carrier. The vaccine may be administered through various routes, including but not limited to, oronasally, subcutaneously, and intramuscularly.

The invention also contemplates a method of detecting a hemorrhagic feline calicivirus (hFCV) antibody in a biological sample. The method includes contacting the biological sample with an antigen of a hFCV and detecting the formation of an immune complex. Optionally, the antigen is a whole virus.

The invention further encompasses a composition comprising an isolate of a hemorrhagic feline calicivirus (hFCV) having all the distinguishing characteristics of a virus deposited under ATCC Accession Numbers PTA-5798 (FCV-Kaos) and PTA-5797 (FCV-Ari).

DETAILED DESCRIPTION OF THE INVENTION

Definitions

A "hemorrhagic feline calicivirus" (FCV) refers to an, a typical, unusually virulent and highly contagious form of feline calicivirus (FCV) that results in a hemorrhagic fever syndrome in cats. An hFCV strain of the invention cannot be neutralized by antibodies to universal vaccine strains (e.g., FCV-F9), thus, treatment of cats with antiserum against FCV-F9 achieves negligible protection against infection with hFCV. An hFCV of the invention can be identified by the relative inability of antiserum against FCV-F9 to neutralize virus in a standard in vitro assay as described for example in Pedersen et al. *Vet. Microbiol.* (2000) 73:281-300. A virus neutralizing antibody assay suitable for this purpose is described in detail below. Briefly, virus neutralizing titers are determined by reacting serial dilutions of serum from a cat vaccinated with FCV-F9 with a constant amount of an FCV to be tested. Cyotpathic effect (CPE) against Crandell feline kidney cells (CrFK) is used to determine viral infectivity. The last dilution containing any detectable CPE was read as endpoint. A CPE at a dilution of less than 1:16 of anti-FCV-F9 antiserum of an isolate capable of causing fatal systemic disease, is an indication that the FCV is an hFCV of the invention.

An "immunologically effective amount" refers to an amount of an immunogen sufficient to induce a detectable humoral or cellular immune response in an animal.

An "attenuated" virus refers to a virus that is either unable to colonize a host, unable to cause disease in a host or causes significantly reduced disease symptoms in a host. Attenuated viruses typically lack a genetic component involved in host colonization or pathogenicity.

A "protective immune response," as used herein, refers to a cellular or humoral immune response that prevents or delays infection or disease caused by a specified pathogen.

A "biological sample" refers to any sample obtained from a living or dead organism. Examples of biological samples include biological fluids and tissue specimens. Examples of tissue specimens include fetal brain tissue, spinal cord, and placenta. Examples of biological fluids include blood, serum, plasma, urine, ascites fluid, cerebrospinal fluid and fetal fluid.

A) Feline Hemorrhagic Calicivirus FCV-Kaos

The instant invention relates to novel hemorrhagic feline calicivirus (hFCV) strains such as FCV-Kaos causing a highly contagious and fatal hemorrhagic fever syndrome. The virus strains causing outbreaks of hFCV are genetically distinct, but cause similar disease and vaccine resistance. The novel FCV-Kaos strain arises by spontaneous mutation from high density cat populations and then spreads readily to associated cats. In addition, FCV-Kaos is not neutralized by antibodies to the routine FCV vaccine strains (e.g., FCV-F9). Hence, vaccinated cats are not protected against this mutant strain. The mortality that is associated with this new strain is as high as 50% in effected animals. The source of the mutant strain is often kittens from shelters that are seen in private practices. The virus spreads quickly via contact (e.g., cat-to-cat, person-to-cat) to client owned animals. It is predicted that this virus may extend into the general population of cats (e.g., 70,000,000 pet cats in the U.S.), likely affecting hundreds of thousands of animals unless a vaccine is available to immunize the general cat population. Thus, it is an object of this invention to provide a vaccine that will induce broader immunity than so far available through current calicivirus vaccines to prevent viral infections by FCV-Kaos. FCV-Kaos has been deposited with the American Type Culture Collection under accession number PTA-5798.

One embodiment of the invention provides an immunogenic composition for immunization against a viral infection by FCV-Kaos, wherein the immunogenic composition comprises an immunologically effective amount of the virus and a physiological carrier. Optionally, the vaccine includes an adjuvant. The FCV-Kaos strain may be live, attenuated, or inactivated.

Symptoms of the FCV-Kaos strain include, but are not limited to, high fever (i.e., highly contagious and fatal hemorrhagic fever syndrome); facial and limb edema (e.g., swelling); ulceration (e.g., crusting and focal hair loss) especially on the face, muzzle and pinnae; icterus; pancreatitis; dyspnea; DIC (disseminated intravascular coagulation); death in severe cases (death may occur in some cats with minimal preceding signs); hyperbilirubinemia; hyperglucosemia; increased CPK (creatinine phosphokinase); nasal and ocular discharge; oral ulceration; anorexia; and depression.

In particular, the mutant strain causes a hemorrhagic-like fever in cats. Cats develop this high fever, become depressed, often have oral and nasal discharge, and commonly develop swellings on their face, trunk, and lower extremities. Cats with milder signs sometimes recover within a few days, while cats with severe signs often die despite extensive symptomatic treatment. More specifically, cats present variably with approximately 50% having facial and paw edema; 90% being febrile (as high as 106 F); 50% with classical signs of upper respiratory tract infection (UR1) such as ocular and nasal discharge, conjunctivitis, and vesicular or ulcerative stomatitis; 20% with icterus; and 30-40% with hemorrhage such as from nose and feces. Necropsy findings are also variable, including lung consolidation and pneumonia in 80% cats; hepatomegaly in 50% cats; pancreatitis in 10% cats; and pericarditis in 10% cats.

The incubation period for this strain in most cases is between 1-5 days. However, a few cases appear to have developed up to 12 days after the last known exposure. Cats of all ages, including fully vaccinated cats, are affected by this strain. A significant percentage of cats may continue to shed virus for some time after recovery from clinical signs, as is the case with other strains of feline calicivirus. Therefore, cats may still be infectious to others following early recovery.

FCV-Kaos, which is one example of a hFCV strain, may be present systemically, and may be shed in feces and in nasal, ocular and oral secretions. Transmission of FCV-Kaos occurs easily. Spread of disease is facilitated by client and technician traffic between hospitals. The virus can be very readily spread by fomites (i.e., any object that functions to transfer infection contaminated by pathogens from a diseased source) as well as direct transmission. It can be carried for at least several hours on contaminated hands, clothing, instruments, shoes, and the like. This virus may be carried home on clothing contaminated by handling infected cats, resulting in infection of cats that were never directly exposed to a sick cat (i.e., person-to-cat transmission). Droplet transmission is possible over as long as a distance as 1-2 meters. Although, FCV-Kaos may be carried through ventilation systems on dust and hair, airborne transmission over distances greater than a few feet is not normally associated with this strain. Recognition of the infectious nature of the disease may often be delayed because a case is not seen at the hospital where the disease first spreads, and subsequent spread to other hospitals occurs when owners take cats infected at one hospital to another hospital for treatment. Thus, careful attention to prevention of fomite transmission is important to prevent spread of FCV-Kaos. hFCV can persist in the environment in a dried state at room temperature (20° C.) for up to 28 days. This may play a role in the seemingly delayed transmission of infection.

hFCV strains, such as FCV-Ari and FCV-Kaos, arise most often from multiple cat environments such as shelters and catteries. Kittens borne to persistently infected mothers may shed virulent hFCV while showing minimal clinical signs themselves compared to adult cats. Hence, there may be a role for kittens in propagating hFCV. The high proportion of kittens, high population turnover and constant influx of vulnerable animals common to many shelters and rescue groups further increases the opportunity for high level virus replication, host switching, viral spread, replication and mutation. Generally, methods of spreading the disease have implications for hFCV control methods. In particular, mildly affected animals can play an important role in disease transmission (e.g., an apparently well cat is released home and his littermate shortly thereafter develops the fatal disease).

Cats of all ages are susceptible to FCV-Kaos, but adults are at significantly greater risk than kittens for severe disease and death. This is often the case when the reaction of the immune system is correlated with the severity of the disease. Vaccinated cats (e.g., FCV-F9) can be infected and suffer severe disease and death from FCV-Kaos, as is commonly the case. Strains of hFCV are generally vaccine resistant. Mutations that causes hemorrhagic strains of FCV may be linked to a change in antigenic structure that confers vaccine resistance. Viral culture, cDNA sequencing and serology of exposed cats allows for recognition of a wide range of clinical manifestations of hFCV disease, including mild and subclinical infections. Viral isolation from oropharyngeal swabs by culture and PCR proves to be a sensitive method of diagnosing disease when samples are obtained during acute infection or at necropsy. Positive cultures can be obtained even from asymptomatic cats soon after exposure. Since sensitivity of viral isolation decreases substantially later in the disease, a single negative swab cannot rule out low level excretion. Serology is useful to confirm a history of exposure, and is usually sensitive and specific based on any samples obtained during an outbreak.

Isolates of FCV-Kaos are closely related to one another, but are not closely related to FCV-Ari, another strain of hFCV which has been characterized by cDNA sequencing as described in Pedersen et al *Vet. Microbiol.* (2000) 73:281-300. This may indicate that the mutation causing hFCV disease is different in each case. Because FCV is commonly isolated from the oral cavity of clinically healthy cats and cats with URI, positive viral culture or PCR from a cat with signs of vasculitis should not be considered diagnostic of hFCV disease without the support of cDNA sequencing demonstrating a distinct strain in more than one affected cat.

Some cats which survived FCV-Kaos infection may become chronic carriers, as commonly occurs with other strains of FCV. For example, cats infected with FCV-Ari are known to be culture positive up to 10 weeks after infection. Also, shedding of FCV-Kaos may persist at least 16 weeks in some cats. Hence, chronic carriers could pass hFCV strains to other cats long after recovery from clinical signs. Widespread susceptibility to FCV-Kaos infection exists regardless of age, health or vaccination status. Although, a highly virulent infection may kill off its hosts faster than disease can spread, in the outbreak documented herein (see Examples) at least 32 cats survived and some continued to shed virus indistinguishable from virulent FCV-Kaos. If the virus retains the same virulence and ease of spread that is observed early in an outbreak, it is likely that additional outbreaks would arise from this potential reservoir of infected cats. Mutation that lead to hFCV may revert during passage to yield a less or more virulent strain, and variant strains arise in persistently infected cats. Thus, FCV-Kaos infection poses a significant risk to the cat population and may lead to further serious outbreaks and spreading of disease.

B) Feline Hemorrhagic Calicivirus FCV-Ari

The instant invention also relates to a novel hemorrhagic feline calicivirus (hFCV) strain such as FCV-Ari, an a typical and highly contagious FCV. FCV-Ari infection in cats manifests in its severest form by a systemic hemorrhagic-like fever that is similar to the one observed with FCV-Kaos infection. The new isolate, FCV-Ari, can be partially neutralized at negligible to low titer by antiserum against the universal FCV-F9 vaccine strain. Cats immunized with FCV-F9, and then challenge-exposed shortly thereafter with FCV-Ari, develop a slightly milder self-limiting form of the disease, indicating a low partial protection, compared to FCV-Kaos (supra). However, antibodies against the universal FCV-F9 vaccine strain do not significantly cross-react with FCV-Ari and immunization with FCV-F9 provides only a small measure of immunity for cats. A large proportion of previously vaccinated cats (i.e., immunized with parenteral FCV-F9 vaccine) die soon after exposure to FCV-Ari.

The disease caused by FCV-Ari appears to target blood vessels, as evidenced by the severe edema (sometimes hemorrhage) in subcutaneous tissues and lungs and local necrosis of skin and adipose tissues. Loss of vascular integrity relates to a significant drop in serum proteins, icteric serum (from breakdown of extravasated red blood cells), variable thrombocytopenia, and coagulopathies. There are also elevations in CPK that indicate myonecrosis. Generally, features of this disease include high mortality, the tendency to cause more severe disease in older animals, the ease of spread, the acute nature, hepatocyte tropism, and widespread vascular disease. It is noteworthy that the infection may persist in cats that are dying, i.e., the virus is still present in the blood of a cat at the time of death. FCV-Ari is a highly virulent strain that is most destructive to older animals. Although, inherent resistance factors may also play a role, in that, some cats develop milder self-limiting disease while others are devastated by infection. FCV-Ari, symptoms and disease are described in detail in Pedersen et al., *Vet. Microbiol*. (2000) 73:281-300 which is incorporated by reference herein. FCV-Ari has been deposited with the American Type Culture Collection under accession number PTA-5797.

One embodiment of the invention provides an immunogenic composition for immunization against a viral infection by FCV-Ari, wherein the immunogenic composition comprises an immunologically effective amount of the virus and a physiological carrier. Optionally, the vaccine includes an adjuvant. The FCV-Ari strain may be live, attenuated, or inactivated.

Another embodiment of the invention provides an immunogenic composition for immunization against a viral infection by hFCV, not including FCV-Ari, wherein the immunogenic composition comprises an immunologically effective amount of the virus and a physiological carrier. Optionally, the vaccine includes an adjuvant. The FCV-Ari strain may be live, attenuated, or inactivated.

C) Immunogenic Compositions

One aspect of the invention provides for a method of immunizing a cat against hFCV strains such as FCV-Kaos and FCV-Ari which comprises administering to the cat an effective dose of an immunogenic composition of the invention. In a preferred embodiment of the invention, attenuated or killed FCV-Kaos virus is combined or mixed with various solutions and other compounds as are known in the art. In another preferred embodiment of the invention, attenuated or killed FCV-Ari virus is combined or mixed with various solutions and other compounds as are known in the art. Immunogenic compositions may be prepared as injectables, as liquid solutions or emulsions. The viral strains of the invention may be mixed with pharmaceutically-acceptable excipients. Excipients may include water, saline, dextrose, glycerol, ethanol, and combinations thereof. The vaccine may further contain auxiliary substances such as wetting or emulsifying agents, pH buffering agents, or adjuvants to enhance the effectiveness of the vaccines.

Immunogenic compositions of the present invention may comprise the whole virus and/or virally-infected cell lines. The virus may be wholly or partially inactivated and utilized as an immunogen in the composition. Partial inactivation may be achieved by passage at elevated temperatures or by contact with mutagens, such as ultraviolet light, ethyl methanesulfonate, and the like. Complete inactivation may be achieved by contact with other agents, including formalin, paraformaldehyde, phenol, alpha-lactopropionate, ultraviolet light, heat, psorlens, platinum complexes, ozone and other viricidal agents.

In addition to whole virus, viral proteins or peptides may also be used in the preparation of subunit vaccines prepared by known techniques. Those of skill will readily recognize that it is only necessary to expose a mammal to appropriate epitopes in order to elicit effective immunoprotection. The epitopes are typically segments of the whole protein. Thus, it is possible to prepare immunogenic compositions of the invention comprising isolated proteins or polypeptides as immunogens in place of the attenuated or killed whole virus. One of skill will recognize that such immunogens can be prepared using recombinant techniques. It is also routine to alter a natural protein's primary structure to create derivatives embracing epitopes that are identical to or substantially the same as (immunologically equivalent) the naturally occurring epitopes. Such derivatives may include peptide fragments, amino acid substitutions, amino acid deletions and amino acid additions within the natural amino acid sequence for the select target protein. For example, it is known in the protein art that certain amino acid residues can be substituted with amino acids of similar size and polarity without an undue effect upon the biological activity of the protein.

Polypeptides displaying antigenic regions capable of eliciting protective immune response are selected and incorporated in an appropriate carrier. Alternatively, an immunogenic portion of a viral protein or proteins may be incorporated into a larger protein by expression of fused proteins. The preparation of subunit vaccines for other viruses is well known and is described in various references, including Lerner et al. (1981) *Proc. Natl. Acad. Sci. USA* 78:3403 and Bhatanagar et al (1982) *Proc. Natl. Acad. Sci. USA* 79:4400. See also, U.S. Pat. No. 4,565,697 (where a naturally-derived viral protein is incorporated into a vaccine composition); U.S. Pat. Nos. 4,528,217 and 4,575,495 (where synthetic peptides forming a portion of a viral protein are incorporated into a vaccine composition). Other methods for forming vaccines employing only a portion of the viral proteins are described in U.S. Pat. Nos. 4,552,757; 4,552,758; and 4,593,002.

The vaccines prepared as described above may be administered in any conventional manner, including oronasally, subcutaneously, intraperitoneally or intramuscularly, except that oronasal administration will usually not be employed with a partially inactivated virus vaccine. Adjuvants will also find use with subcutaneous and intramuscular injection of completely inactivated vaccines to enhance the immune response. The preparation of viral vaccine compositions optionally employing adjuvants is described in numerous standard references, such as Remington's Pharmaceutical Sciences, Mack Publishing Co., Easton, Pa., 16th ed., 1982.

The dosage form and immunogen content of the compositions of the invention will vary depending on the nature of the immunogen (i.e., whole virus, infected cell, or subunit) and the route of administration. Usually, a single dose will have a total volume including carrier, adjuvant, and any other components, in the range from about 0.1 ml to about 5 ml, more usually being from about 0.5 ml, more usually being from about 0.5 ml to about 3 ml. The amount of inactivated or attenuated whole virus in each dose will usually be in the range from about 0.1 mg to about 5 mg, usually being from about 0.2 mg to 2 mg. (For inactivated virally-infected cell lines, each dose may typically contain from about 10.sup.6 to 10.sup.8 cells, usually about 5.times.10.sup.6 to 5.times.10.sup.7 cells.)

The number and timing of the inoculations will be sufficient to elicit the desired immunoprotective response against subsequent challenge by hFCV (e.g., FCV-Kaos, FCV-Ari). Usually, there will be at least two inoculations spaced at least one week apart, more usually being from two to 10 inoculations spaced over a period from two to thirty weeks. Often, a final inoculation may be administered at some longer interval following an initial series of administrations. The selection of optimum administration patterns for a particular vaccine formulation is well within the skill in the art.

The compositions of the invention can be formulated for oronasal delivery. Formulations suitable for nasal administration, wherein the carrier is a solid, include a coarse powder having a particle size, for example, in the range of about 10 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient. Various ways of such administration are known in the art. The pharmaceutical formulation for nasal administration may be prepared as solutions in saline, employing benzyl alcohol or other suitable preservatives, absorption promoters to enhance bioavailability, fluorocarbons, and/or other solubilizing or dispersing agents known in the art. The unit dosage for nasal administration can be from 1 to 3000 mg, e.g., 10 to 1000 mg, or 1 to 10 mg of active ingredient per unit dosage form.

Vaccines of the invention may be combined with other vaccines for the same or other diseases to produce multivalent vaccines. A pharmaceutically effective amount of the immunogen can be employed with a pharmaceutically acceptable carrier such as a protein or diluent useful for the vaccination of mammals, particularly cats. Other vaccines may be prepared according to methods well-known to those skilled in the art.

Examples of other vaccines, including other cat vaccines, that can be combined with attenuated or killed FCV Kaos or FCV-Ari include, but are not limited to, panleukopenia virus antigens, feline herpesvirus I antigens, leukemia virus antigens, and rabies antigens.

D) Assays for Detecting hFCV

The hFCV virus strains of the instant invention (e.g., FCV-Kaos, FCV-Ari) and antibodies that specifically bind to them can be detected and/or quantified using any of a number of well recognized immunological binding assays. For a review of the general immunoassays, see also Methods in Cell Biology: Antibodies in Cell Biology, volume 37 (Asai, ed. 1993); Basic and Clinical Immunology (Stites & Terr, eds., 7th ed. 1991). Immunological binding assays (or immunoassays) typically use an antibody that specifically binds to a protein or antigen of choice. The antibody may be produced by any of a number of means well known to those of skill in the art and as described above. Alternatively, a protein or antigen of choice may be used to bind antibodies in the serum of an infected animal. The protein or antigen may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled antigen or a labeled antibody. Alternatively, the labeling agent may be a third moiety, such a secondary antibody, which specifically binds to the antibody/antigen complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., J. Immunol. 111: 1401-1406 (1973); Akerstrom et al., J. Immunol. 135:2589-2542 (1985)). The labeling agent can be modified with a detectable moiety, such as biotin, to which another molecule can specifically bind, such as streptavidin. The streptavidin may be bound to a label or detectable group as discussed below. A variety of detectable moieties are well known to those skilled in the art.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADSTM), fluorescent dyes (e.g., fluorescein isothiocyanate, Texas red, rhodamine, and the like), radiolabels (e.g., $^3H$, $^{125}I$, $^{35}S$, $^14C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple calorimetric labels may be detected simply by observing the color associated with the label. Thus, in various dipstick assays, conjugated gold often appears pink, while various conjugated beads appear the color of the bead.

A number of assay formats are well known. The assays can be either competitive or non-competitive assays. Typical assays will be carried out in the ELISA format. Western blot (immunoblot) analysis can be used to detect and quantify the presence of the viral antigens in a sample. Other assay formats include liposome immunoassays (LIA), which use liposomes designed to bind specific molecules (e.g., antibodies) and release encapsulated reagents or markers. The released chemicals are then detected according to standard techniques (see, Monroe et al., Amer. *Clin. Prod. Rev.* 5:34-41 (1986)).

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Nucleic acid-based assays can also be used to detect the presence of FCV-Kaos DNA and RNA in a sample. Such assays include numerous techniques known to those skilled in the art, such as Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis.

E) EXAMPLES

The following specific examples are intended to illustrate the invention and should not be construed as limiting the scope of the claims.

An outbreak of FCV-Kaos occurred among cats at three veterinary practices in the area of Los Angeles, Calif. during June and July of 2002. A hemorrhagic fever like syndrome was observed, with affected cats showing signs of vasculitis, facial and limb edema, and multiple organ involvement in addition to more commonly observed signs of caliciviral respiratory infection. A total of 54 cases were documented. Overall mortality was 40%, and mortality in adult cats (>6 months) was 59%. Adult cats were more likely than kittens to suffer severe disease or death (odds ratio 9.56, CI=2.82–32.39, p<0.001). The attack proportion was 94%. 21% of cases were mild or subclinical. Many affected cats had been vaccinated against feline calicivirus, however, antibodies to the vaccine strain FCV-F9 did not neutralize FCV-Kaos. In fact, at least twenty-six (48%) of the affected cats had a history of vaccination against feline herpes virus, calicivirus, and panleukopenia virus. Spread of FCV-Kaos occurred readily within and among hospitals and homes via fomites and movement of infected cats. Examples 1-8 (*vide infra*) provide a detailed description of FCV-Kaos outbreak, -symptoms, -illness, -pathology, and -analysis. Example 9 (vide infra) describes the earlier outbreak of a similarly virulent and highly contagious strain, FCV-Ari.

Example 1

Data Collection

The information on FCV-Kaos cases was collected by interviews conducted in-person and by phone, and by examination of medical records. Three veterinary practices and one rescue group were affected by the FCV-Kaos strain. Each affected practice was visited and all available records of suspect cases were reviewed. The information was collected on all cats hospitalized as inpatients during the outbreak, whether or not they showed signs of infection. A written summary of all kittens present within the rescue group's foster home network at the time of the outbreak was provided by rescue group personnel.

Example 2

Case Definition

The FCV-Kaos cases were classified as confirmed-, suspect-, or possible.

A "confirmed" case was defined as any of the following:

(a) A cat from which FCV-Kaos was isolated and genetically sequenced.

(b) A cat exposed to a case confirmed by genetic sequencing which exhibited either sudden death or edema of the face or feet not explained by other causes, and with one or more additional signs of caliciviral infection (e.g., fever, oral ulcers, ocular or nasal discharge, limping).

A "suspect" case was defined as any of the following:

(a) A cat exposed to a confirmed case, in which sudden death or edema or sores/alopecia/ulceration of the face or feet with other signs of caliciviral infection was reported but not confirmed by a veterinarian or for which other causes were not ruled out.

(b) A cat exposed to a confirmed case and seropositive to FCV-Kaos but with no abnormal clinical signs reported.

A "possible" case was defined as follows:

(a) A cat exposed to a confirmed case and reportedly febrile, with other signs of upper respiratory infection (e.g., oral ulcers, ocular or nasal discharge, anorexia) but without edema or death and for which no viral culture or serology was available.

Example 3

Clinical Signs and Pathology

Fever was the most commonly reported clinical symptom in cats, affecting 44/54 animals (81%). Median temperature was 40.6° C. (105.1° F.) with a range from 39.4° C. to 42.4° C. (103.0° F. to 106.5° F.). Either limb and/or facial edema was reported in 28/54 (52%) of cases (limb edema was reported in 25 cases; and facial edema in 14 cases). In decreasing order of frequency, other abnormalities reported were: oral ulcers (25/54, 46%); nasal discharge (16/54, 30%); dyspnea (9/54, 17%); sores, crusting or alopecia of the face, pinnae, or feet (9/54, 17%); ocular discharge/conjunctivitis (6/54, 11%); clinically apparent jaundice (6/54, 11%); pleural effusion (5/54, 9%); diarrhea (4/54, 7%); vomiting (4/54, 7%); and limping (3/54, 6%). The hemorrhagic fever included signs that were characteristic of vasculitis and frank hemorrhage. Frank hemorrhage was observed in two cases (from the nose in one case, and from the nose and rectum in another case).

Severity of illness ranged from no signs at all to fatal illness. No abnormalities were observed in 3/54 cases (6%) that were considered to be infected (based on positive viral culture and sequencing). In 8/54 cases (15%), only mild signs were observed, limited to oral ulcers, nasal/ocular discharge and fever <104° F. Moderate signs were reported in 8/54 cases (11%), including fever >104° F., lethargy/inappetance for >1 day, sores/crusting/pustules of skin, with ocular/nasal discharge and/or oral ulcers. Severe signs including edema, respiratory distress and/or death were reported in 35/54 (65%) cases; 13 of the 35 cats with severe signs survived.

The date of first exposure was determined in 17 cases. For these cases, the median time from exposure to first observation of signs was 4 days, with a range of 1 to 12 days. The longer apparent incubation times occurred in cats secondarily exposed by another sick cat in the home. In cats exposed as inpatients, the longest time observed between exposure and observation of signs was 5 days. One cat developed signs up to 34 days after his first probable exposure. He may have been exposed a second time between 2-15 days prior to the onset of symptoms.

Blood chemistry panels were available for 10 cases. Abnormal findings on blood chemistry included hyperbilirubinemia in 6/10 cases (range 0.6-3.9 mg/dl, reference range=0.1-0.4 mg/dl); hypoalbuminemia in 5/10 cases (range 1.1-2.1 g/dl, reference range 2.5-3.9 g/dl); elevated aspartate aminotransferate (AST) in 3/10 cases (range 103-223 IU/L, reference range 10-100 IU/L); mildly elevated alanine aminotransferase (ALT) in 2/10 cases (range 102-116 IU/L, reference range 10-100 IU/L); and elevated creatine phosphokinase (CPK) in 5/10 cases (range 639-10930 IU/L, reference range 56-529 µl/L).

Complete blood counts were available for 8 cases. 3/8 cases had a mild neutrophilia (range 8549-11616 cells/µl, reference range 2500-8500 cells/µl), and 5/8 had a mild to moderate lymphopenia (range 180-1188 cells/µl, reference range 1200-8000 cells/µl). Hematocrit was slightly decreased in 2/8 cases (25%, reference range 29-48%).

Gross necropsy results were available for five cats. In all cats there was abundant bright yellow subcutaneous edema most markedly affecting the face and limbs. In two cats dependent edema extended along the thoracic wall and affected the entire inguinal and axial regions. Conjunctiva were red and swollen with crusted material adhered to the medial canthi. Ulcers were present on all cats although sites and extent were variable. Three cats had circumferential ulceration at the junction between the paw pads and haired skin. In two cats there were 0.4 cm diameter to coalescing ulcers of the dorsal, lateral and ventral tongue surfaces. In two cases, although the tongue appeared unaffected there was ulceration of the septum of the nares and of the haired skin overlying the nose. In all cats there was up to 100 ml of pale red, slightly opaque fluid within the abdominal and thoracic cavities and in one cat there was extensive pericardial fluid of similar character. In two cases, there was minimal and multifocal omental fat necrosis. Histologic analysis revealed that the ulcerations in all cases corresponded to microscopic vast regions of epithelial necrosis and ulceration with minimal inflammation. The superficial dermis underlying this region was often disrupted and expanded by edema and cell debris. The remainder of the dermis was minimally affected excepting occasional extension of necrosis into follicular epithelium. In three cats massive or centrilobular, peracute hepatic necrosis was present.

Example 4

Serology

Serum was collected from 19 cats that had survived infection with FCV-Kaos, and from 2 kittens that may have been indirectly exposed but were presumably uninfected (based on absence of clinical signs and negative viral culture). Serum samples were collected 1-6 weeks after the estimated time of infection or exposure. Virus neutralizing titers were determined by reacting four-fold serial dilutions of serum with a constant amount of virus. The dilutions of serum used were 1:4, 1:16, 1:64, 1:256, 1:1024, 1:4096, and 1:16,384. Crandell feline kidney cells (CrFK) were used in 96-well plates for the titration.

50 µl of patient serum was diluted serial four fold (1:4 to 1:16,384, supra) with tissue culture medium in 96 well culture plates. 50 µl of tissue culture medium containing approximately 1000TCID$_{50}$ (1000 tissue culture infectious dose) of FCV was then added to each well and incubated for 1-2 hours at 37° C. The serum/virus mixture from each well was then transferred into corresponding wells of a culture plate containing 1-2 day old, just confluent, CrFK cells. Each serum was tested against three virus isolates: FCV-F9 (vaccine strain), FCV-Kaos, and FCV-case 53 (an unrelated field isolate from case 53). The plates were incubated for 24 hours and observed under an inverted microscope for typical FCV CPE (cytopathic effect). The last well containing any detectable CPE was read as endpoint. A CPE at a dilution of 1:16 or greater was considered a positive result.

Results of serology are shown in Table 1 below. All cats with either confirmed FCV-Kaos infection or housed in the same cage as an FCV-Kaos positive cat were seropositive to FCV-Kaos. All cats housed in the same cage as case 53 were seropositive to FCV-53, as were two cats in group 6 with no known history of exposure to case 53. The cats in group 2 were not directly exposed to case 53 or FCV-Kaos. These cats never showed clinical signs of infection, were culture negative for FCV infection, and were seronegative for both viral strains. There was no evidence of cross-reaction between FCV-F9 and either FCV-Kaos or FCV-53 (virus neutralizing antibody levels <1:4).

TABLE 1

| | | | | Antibody Titer to FCV Strain | | | |
|---|---|---|---|---|---|---|---|
| Case # | Group[1] | Vaccine Status | Severity | FCV-case53[2] | Vaccine (FCV-F9) | FCV-Kaos | FCV Strain Isolated |
| 53 | 1 | Yes | 3 | 1:16 | 1:16 | 1:16 | FCV-case53, FCV-Kaos[3] |
| 41 | 1 | no | 4 | 1:256 | 1:16 | 1:256 | FCV-Kaos |
| 54 | 1 | no | 2 | 1:256 | 1:16 | 1:64 | FCV-Jengo[4] |
| 52 | 1 | Yes | 3 | 1:64 | 1:64 | 1:16 | None[5] |
| 51 | 1 | Yes | 2 | 1:256 | 1:16 | 1:64 | None |
| 40 | 1 | Unknown | 3 | 1:256 | 1:16 | 1:16 | None |
| 50 | 1 | Yes | 2 | 1:1024 | 1:16 | 1:64 | None |
| R1[6] | 2 | Yes | 0 | 1:4 | 1:64 | <1:4 | None |
| R2[6] | 2 | Yes | 0 | <1:4 | 1:4 | <1:4 | None |
| 32 | 3 | Yes | 2 | <1:4 | 1:4 | 1:256 | None |
| 33 | 3 | Yes | 1 | 1:4 | 1:4 | 1:64 | FCV-Kaos |
| 31 | 4 | yes | 3 | <1:4 | 1:16 | 1:64 | None |
| 35 | 5 | Yes | 4 | <1:4 | 1:64 | 1:256 | FCV-Kaos |
| 36 | 5 | Yes | 4 | 1:4 | 1:16 | 1:1024 | FCV-PM |
| 34 | 5 | Yes | 4 | <1:4 | 1:16 | 1:256 | None |
| 12 | 6 | Yes | 4 | 1:4 | 1:16 | 1:64 | None |
| 18 | 6 | Yes | 4 | 1:4 | 1:4 | 1:64 | FCV-Kaos |
| 9 | 6 | Yes | 4 | 1:4 | 1:64 | 1:256 | None |
| 10 | 6 | Unknown | 4 | 1:4 | 1:4 | 1:256 | FCV-Kaos |
| 11 | 6 | Yes | 4 | 1:16 | 1:64 | 1:256 | None |
| 21 | 6 | Unknown | 4 | 1:64 | 1:16 | 1:256 | FCV-Kaos |

[1]Groups 1-5 were kittens from the rescue group. Each group was housed in a separate cage, but all were in the same general area and cared for by the same caretakers. Group 6 cats were from a practice; the cats were housed in isolation in separate cages.
[2]Field strain of calicivirus isolated from one rescue kitten during outbreak and associated with mild URI signs.
[3]FCV-case53 isolated before exposure to case 41; FCV-Kaos isolated after exposure to case 41.
[4]Field strain of calicivirus isolated from 2 rescue kittens during outbreak, wherein both kittens had signs of severe liver disease.
[5]No FCV isolated on 2-5 attempts over 10 week follow up period.
[6]R1 and R2 were never symptomatic or culture positive for calicivirus infection, and were therefore not considered cases.

Example 5

Histology

All tissue samples were fixed in 10% neutral buffered formol-saline. Selected tissues were embedded in paraffin, sectioned at 4 μm, and mounted on positive-charged glass slides (Superfrost/plus, Fischer Scientific, Pittsburgh, Pa.). Tissue sections were stained with hematoxylin and eosin (HE) for routine light microscopy examination.

Example 6

Viral Isolation, Culture, and Sequencing 77 cultures were provided. 19/77 cultures were from cats sampled once, and 18/77 were from cats sampled 2-5 times at 1-3 week intervals. Viral isolation performed at the peak of clinical signs was positive in 88% (15/17) of cases. In some of the cats sampled repeatedly, intermittent and persistent shedding was observed.

Caliciviruses were isolated from cat serum and cultured on a confluent monolayer of Crandell feline kidney cells (CrFK) from freshly harvested spleen or lung, EDTA-anticoagulated whole blood, nasal discharge, or oropharyngeal secretions collected on sterile cotton swabs and transported in sterile saline solution or in sterile saline with the addition of 0.02 mg/ml of penicillin and amikacin. Cells were maintained at 37° C. in air with 5% $CO_2$ and growth media containing one half Liebovitz L-15 media and one half MEM (Eagle's minimum essential media). The media contained 10% FBS (fetal bovine serum), 100 U penicillin G/ml, and 100 μg streptomycin/ml of media. A viral infection was confirmed by the presence of a characteristic cytopathic effect (CPE) within cells from 12-52 hours. After inoculation, tissue culture fluid was harvested from all infected cells and total RNA was extracted using a kit (Qiagen Tissue Kit, Chatsworth, Mass.). Reverse-transcription/nested-polymerase chain reaction was performed as described in Pedersen, et al, *Vet Microbiol* 73(4):281-300 (2000). All apparently culture-positive isolates were PCR-positive. Fragments were purified by Microcon-50 Columns (Millipore Corp, Bedford, Mass.) and all positive results were confirmed by sequencing, i.e., by automated cDNA sequencing using a sequencing service (Davis Sequencing, Davis, Calif.). Thus, FCV-Kaos was isolated and confirmed by cDNA sequencing. In fact, all positive results were confirmed by cDNA sequencing.

Example 7

Viral Characterization

Viral isolates from symptomatic and exposed cats were sequenced and compared to several field strains of FCV, vaccine strain (FCV-F9), and FCV-Ari (a hFCV strain isolated in a 1998 Northern California outbreak as described in Pedersen et al., *Vet Microbiol* 73:281-300 (2000) (supra). All isolates of FCV-Kaos clustered within a single dade, being genetically distinct from the other strains used for comparison. Isolates of FCV-Kaos were characterized by a three base pair deletion not observed in the other strains.

Example 8

Statistical Analysis of Infected Cats

The data summary was performed in "R" (The R-Development Core Team) which is a language and environment for statistical computing and graphics similar to the S language and environment which was developed at Bell Laboratories (formerly AT&T, now Lucent Technologies). R can be considered as a different implementation of S. There are some important differences, but much of the code written for S runs unaltered under R (Richard A. Becker, John M. Chambers, and Allan R. Wilks. *The New S Language*. Chapman & Hall, London, 1988). Possible associations of cases with age, vaccination status and sex were evaluated by chi-square contingency tests. Univariate evaluation of possible risk factors was performed by calculating odds ratios and confidence intervals (function "odds" on R). Values of $P<0.05$ were considered significant.

The attack proportion for cats either hospitalized concurrently with a case cat for $\leqq 12$ hours or from the same household as a case cat was 94% (47/50). The case fatality proportion overall was 41% (22/54). In cats >1 year old, the case fatality proportion was 59% (19/32), and in kittens <6 months old it was 14% (3/22). Adult cats (>1 year old) had significantly higher odds than kittens (<6 months old) for severe disease or death (odds ratio 9.56, CI=2.82, 32.39, $p<0.001$). Sex was not a significant risk factor for severe disease or death. Few of the cats were known to be unvaccinated; therefore risk associated with vaccination could not be assessed in adult cats. Of the kittens whose vaccine status was known, 7 had received a modified live intranasal vaccine and 11 had received a modified live subcutaneous vaccine. There was no significant difference in likelihood or severity of disease between these two groups of vaccinated kittens.

Example 9

FCV-Ari

In 1998, another outbreak of a highly virulent, vaccine-resistant strain of hFCV, FCV-Ari, associated with a hemorrhagic-like-fever, was reported in Northern California as described in Pedersen et al., Vet Microbiol 73:281-300 (2000) (supra). Death occurred in 33-50% of FCV-Ari infected cats, and this strain proved highly contagious, spreading via contaminated fomites in spite of hygienic precautions in veterinary hospitals and research colonies. Distinctive clinical signs included facial and limb edema in febrile cats, and sudden death in some cases with few preceding signs. Since the report of the 1998 outbreak, at least four focal outbreaks of hemorrhagic fever like FCV have been recognized in Pennsylvania, Massachusetts, Tennessee and Nevada.

Various modifications and variations of the present invention will be apparent to those skilled in the art without departing from the scope and spirit of the invention. Although the invention has been described in connection with specific preferred embodiments, it should be understood that the invention as claimed should not be unduly limited to to such specific embodiments. Indeed, various modifications of the described modes for carrying out the invention which are obvious to those skilled in the art are intended to be within the scope of the claims.

What is claimed is:

1. A composition comprising an isolate of a hemorrhagic feline calicivirus (hFCV) having all the distinguishing characteristics of a virus deposited under ATCC Accession Numbers PTA-5798 or PTA-5797, wherein the distinguishing characteristics comprise inducing a hemorrhagic fever syndrome in cats, and inducing a cytopathic effect against Crandell feline kidney cells in the presence of anti-FCV-F9 antiserum at a dilution of 1:16 or less.

2. The composition of claim 1, further comprising an adjuvant.

3. The composition of claim 1, wherein said virus is killed.

4. The composition of claim 1, wherein said virus strain is attenuated.

5. The composition of claim 1, wherein said virus strain is partially inactivated.

6. The composition of claim 1, wherein said virus strain is a virus deposited under ATCC Accession number PTA-5798.

7. The composition of claim 1, wherein said virus strain is a virus deposited under ATCC Accession number PTA-5797.

* * * * *